United States Patent
Slate et al.

(10) Patent No.: US 6,817,986 B2
(45) Date of Patent: Nov. 16, 2004

(54) JET INJECTOR WITH DATA LOGGING SYSTEM FOR USE IN COMPLIANCE AND DOSE MONITORING PROGRAMS

(75) Inventors: John B. Slate, San Diego, CA (US); Michael W. Burk, San Marcos, CA (US); Lanny A. Gorton, San Diego, CA (US)

(73) Assignee: Avant Medical Corp., San Diego, CA (US)

( * ) Notice: Subject to any disclaimer, the term of this patent is extended or adjusted under 35 U.S.C. 154(b) by 365 days.

(21) Appl. No.: 10/123,870

(22) Filed: Apr. 15, 2002

(65) Prior Publication Data

US 2002/0188419 A1 Dec. 12, 2002

Related U.S. Application Data

(60) Provisional application No. 60/283,840, filed on Apr. 13, 2001.

(51) Int. Cl.[7] .............................................. A61M 5/30
(52) U.S. Cl. ...................... 604/68; 604/115; 604/176; 128/DIG. 1
(58) Field of Search ............................. 604/68, 93.01, 604/115, 130, 137, 174, 176, 181, 187, 131–155, 69–72; 128/DIG. 1, DIG. 12; 600/431–435, 458

(56) References Cited

U.S. PATENT DOCUMENTS

| | | | |
|---|---|---|---|
| 2,706,755 A | | 4/1955 | Krasno |
| 4,114,619 A | * | 9/1978 | Wagner ...................... 604/115 |
| 4,150,672 A | | 4/1979 | Whitney et al. |
| 4,324,127 A | * | 4/1982 | Gazzara et al. ............... 73/1.22 |
| D283,441 S | | 4/1986 | Veelka |
| 4,600,403 A | * | 7/1986 | Wagner ....................... 604/115 |
| 4,788,444 A | | 11/1988 | Williams |
| 4,854,324 A | | 8/1989 | Hirschman et al. |
| 4,921,480 A | * | 5/1990 | Sealfon ........................ 604/65 |
| 4,979,940 A | | 12/1990 | Bobo, Jr. |
| 5,282,785 A | | 2/1994 | Shapland |
| 5,478,316 A | | 12/1995 | Bitdinger |
| 5,536,249 A | * | 7/1996 | Castellano et al. ............ 604/65 |
| 5,593,390 A | | 1/1997 | Castellano |
| 5,925,021 A | | 7/1999 | Castellano |
| 6,241,704 B1 | | 6/2001 | Peterson et al. |
| 6,248,090 B1 | * | 6/2001 | Jensen et al. .................. 604/67 |
| 6,643,537 B1 | * | 11/2003 | Zatezalo et al. ............. 600/432 |
| 2004/0068176 A1 | * | 4/2004 | Kuth ........................... 600/420 |

* cited by examiner

*Primary Examiner*—Anhtuan T. Nguyen
*Assistant Examiner*—Jennifer J. Maynard
(74) *Attorney, Agent, or Firm*—Nydegger & Associates

(57) ABSTRACT

An integral data logging system for a jet injector includes at least one electrical switch that changes state (e.g. from OFF to ON) during an injection procedure. The switch(es) are connected to an electrical circuit having a microprocessor, a clock and an electronic memory. When a switch changes state, this information along with the applicable date and time is recorded in the electronic memory. A communications link is provided to upload the stored data to a remote computer for subsequent manipulation and analysis to determine compliance with a prescribed dosing regimen. In one implementation, the injection duration is logged by using a trigger release switch and an end-of-stroke switch. The end-of-stroke switch is configured to change state after the drive bar of the injector transits through the injector tube. The injection duration is indicative of dose amount and can be used to distinguish between valid and invalid injections.

14 Claims, 5 Drawing Sheets

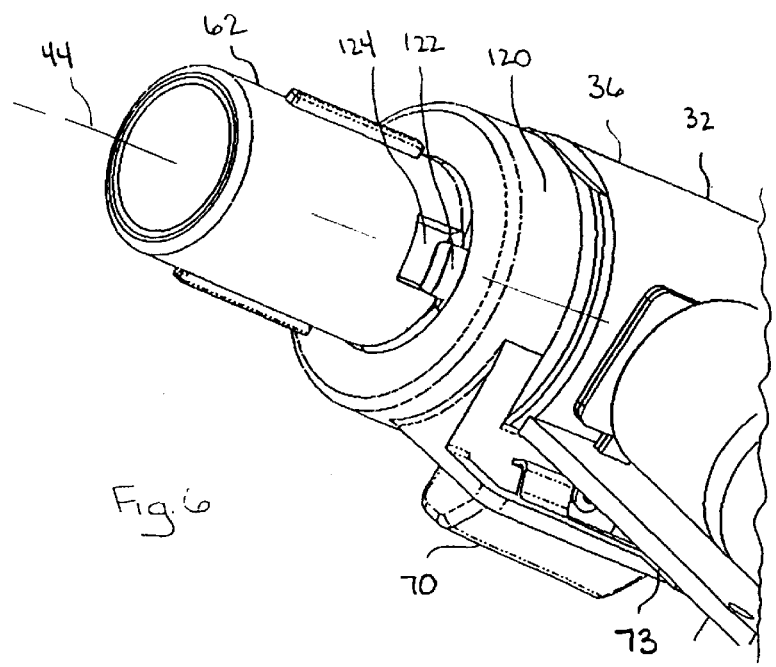
Fig. 6
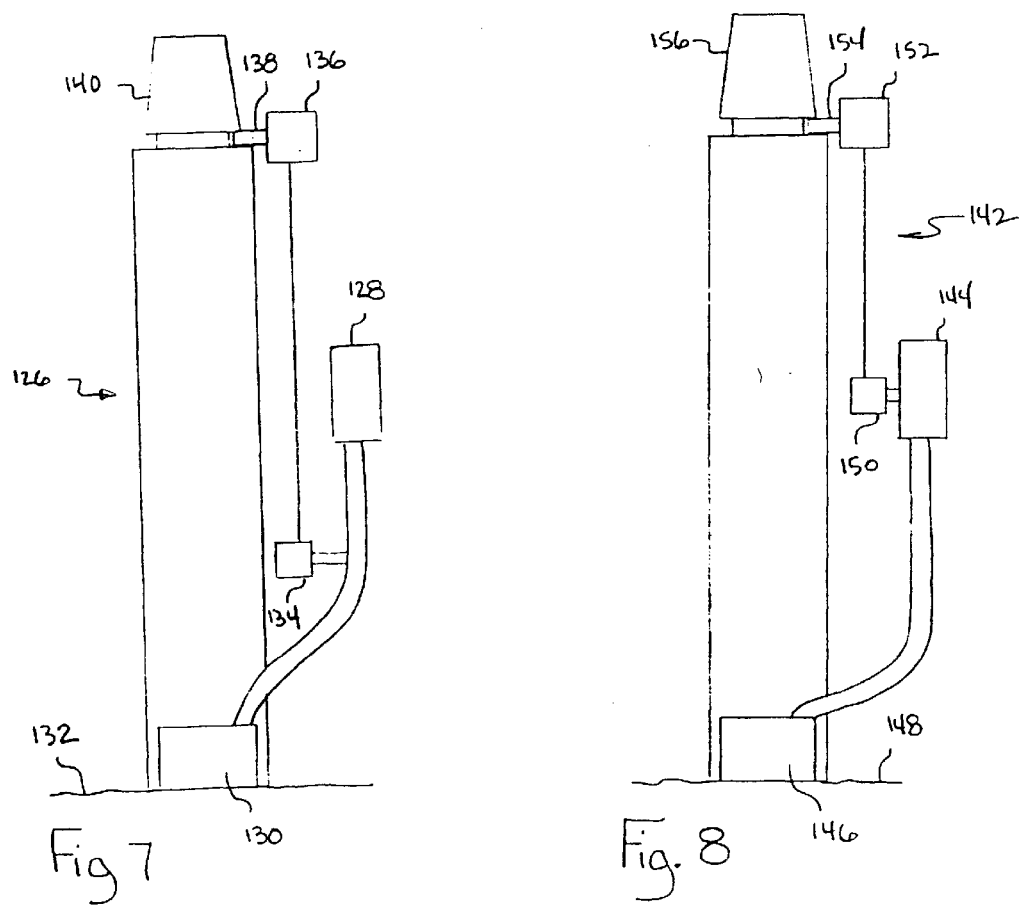
Fig. 7
Fig. 8

JET INJECTOR WITH DATA LOGGING SYSTEM FOR USE IN COMPLIANCE AND DOSE MONITORING PROGRAMS

This application claims the benefit of U.S. Provisional Application Ser. No. 60/283,840 filed Apr. 13, 2001.

FIELD OF THE INVENTION

The present invention pertains generally to injectors for delivering a medicament into a patient. More particularly, the present invention pertains to needle-free jet injectors that are useful as part of a compliance and dose monitoring program. The present invention is particularly, but not exclusively, directed to a jet injector having an integral system capable of producing and recording injection information for subsequent use in determining compliance with a prescribed dosing regimen.

BACKGROUND OF THE INVENTION

Evaluating the effectiveness of drug therapies often requires information regarding dose administration. Some therapies require that the patient comply with a dosing regimen involving frequent injections administered at home or at other sites not observable by a clinician. If the dosing regimens are not followed due to a noncompliant patient, then the effectiveness of the therapy can be significantly diminished and the patient's condition may fail to improve. Money expended on ineffective treatments is wasteful, which is a growing concern with rising health care costs.

An example of a therapy in which compliance is an issue is treating growth hormone deficiency in children. Growth hormone is a very expensive therapy costing over $10,000 per year. If the date and time that the injection is administered can be monitored, then the clinician can provide feedback to the patient or guardian to improve compliance or recommend discontinuing the therapy. Additionally, the insurance carrier may refuse to reimburse patients for therapies that are ineffective due to non-compliance.

In treating some diseases, knowledge of the actual dosing can be important for evaluating whether a particular prescribed regimen is an effective treatment for an individual patient. For example, a physician evaluating a diabetic patient's status benefits from knowing the amount and timing of insulin injections. In this case, correlating the insulin injections with other data, such as glucose measurements, allows the physician to provide the patient with feedback for optimizing their blood glucose control, which is known to have great benefit.

Logging injector data for compliance and dose monitoring can be useful in several clinical applications. As described above, logging injector data can be useful for therapies requiring a fixed drug dosage, such as the treatment of growth hormone deficiency. Additionally, logging injector data is useful for therapies where the dosage is adjusted based on variable patient demand for the drug, such as insulin injections to control blood glucose.

For an effective compliance monitoring system, the validity of an injection together with the date and time that the injector is fired is preferably recorded. Specifically, it is useful to discriminate events that do not represent a valid injection, such as firing the injector: 1) to practice, 2) by mistake, 3) while checking device operation, or 4) as an attempt to fake an injection. In addition, the ability to capture the dose amount administered during a particular injection can be extremely useful in a compliance and dose monitoring program.

The benefits of data logging are not necessarily limited to needle-free systems, intended for self-injection or care sites not observed by clinicians. Data logging and communications could also be beneficial in a hospital or a clinic for entry of the injection into the patient's medical record, for capturing costs, or for inventory control.

In light of the above, it is an object of the present invention to provide a data logging system for a needle-free jet injector capable of producing and recording injection information for subsequent use in determining compliance with a prescribed dosing regimen. It is yet another object of the present invention to provide a data logging system for a needle-free jet injector that can record and store the date, time and dose amount of an injection and can store data from multiple injections. Another object of the present invention is to provide a data logging system for a needle-free jet injector that can distinguish between valid and invalid injections. Still another object of the present invention is to provide a jet injector that prevents invalid injections by preventing a user from firing the injector unless the injector is positioned against the skin. It is another object of the present invention to provide a data logging system for a needle-free jet injector that is integrated with a vacuum control system for the injector. Another object of the present invention is to provide a relatively small and lightweight data logging system that is integral with a needle-free jet injector. It is another object of the present invention to provide a data logging system for a needle-free jet injector that includes a communications link to allow the system to communicate to a standard personal computer and to allow the memory of the system to be accessed and cleared by the personal computer. Still another object of the present invention is to provide a data logging system for a needle-free jet injector that draws a minimal amount of power from the battery during periods of nonuse. Yet another object of the present invention is to provide a data logging system for a needle-free injector which is easy to use, relatively simple to implement, and comparatively cost effective.

SUMMARY OF THE PREFERRED EMBODIMENTS

The present invention is directed to a jet injector that includes an integral data logging system for producing, recording and communicating injection information. This injection information can be subsequently used to determine compliance with a prescribed dosing regimen. For the present invention, the data logging system includes at least one electrical switch that changes state (e.g. from OFF to ON) during an injection procedure. Examples of injector switches that can be used to produce injection information include; a switch configured to change state when an injector safety is released, a switch configured to change state when the injector's vacuum pump is activated, a switch configured to change state when the injector is triggered, a switch configured to change state when the injector's drive bar reaches a pre-selected location within the injector tube and one or more light sensing switches to determine the position of the syringe plunger immediately prior to an injection.

In accordance with the present invention, the switch(es) are connected to an electrical circuit having an electronic memory. When a switch changes state, this information along with the applicable date and time is recorded in the electronic memory. In greater detail, the electrical circuit preferably includes an electrical power source, a microprocessor, a clock, electronic memory and a communications link. Functionally, these electronic components cooperate to record and store injection information that can be subsequently accessed via the communications link and used to determine compliance with a prescribed dosing regimen. More specifically, it is envisioned that a patient will use the injector a plurality of times over a predetermined time interval (e.g. daily for one month). At the end of the interval the patient will provide the injector to a health-care worker who will then upload the data recorded and stored in the electronic memory of the injector via the communications link. For example, the data can be uploaded to a PC at a health-care facility where the data can then be manipulated and analyzed to determine compliance with a prescribed dosing regimen.

In accordance with the present invention, the data logging system can be used to distinguish between valid and invalid injections based on the duration of medicament release from the injector. For example, if a user fires the injector into the air (i.e. an invalid injection) the duration of medicament release will be relatively small as compared to an injection into the skin where the skin provides a back-pressure that slows medicament release. To distinguish between valid and invalid injections, a first switch (hereinafter the trigger release switch) is configured to change state when the firing cap is depressed indicating the start of an injection. Additionally, a second switch (hereinafter the end-of-stroke switch) is configured to change state after the drive bar of the injector transits through the injector tube and comes to rest indicating the end of an injection. In one embodiment, a conductive drive bar contacts a conductive inner barrel after transit through the injector tube to close the end-of-stroke switch.

Also in accordance with the present invention, the electric circuit can be configured to control a vacuum system for the injector in addition to its data logging functions. Specifically, the electric circuit can include a circuit portion that connects an injector vacuum pump to the power source when the user depresses a vacuum activation switch on the injector. In a particular embodiment of the present invention, the vacuum activation switch also functions to release a mechanical safety and arm the trigger of the injector. The electric circuit in this embodiment is further configured to deactivate the vacuum pump when the end-of-stroke switch described above closes.

In another embodiment of the present invention, the injector can be configured to prevent invalid injections (while recording valid injections). In this embodiment, a pre-determined vacuum level downstream of the vacuum pump (indicating that the injector is positioned against a surface such as the skin) is required to arm the trigger of the injector. In one implementation, a safety which prevents movement of the trigger is pneumatically released when the pre-determined vacuum level is achieved. In this embodiment, the user is unable to fire the injector into the air, and thus, only valid injections can occur and are recorded.

In another embodiment of the present invention, one or more light sensing switches are disposed inside the injector tube to determine the position of the syringe plunger immediately prior to an injection. With the initial plunger position, the dose amount for the respective injection can be calculated by the data logging system and used to determine compliance.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 6 is an enlarged, perspective view of the proximal portion of the injector shown in FIG. 2 showing the safety interlock feature of the present invention;

FIG. 7 is a schematic view of an embodiment of the present invention in which the user is prevented from firing the injector unless the tip of the injector is held against a surface;

FIG. 8 is a schematic view of another embodiment of the present invention in which the user is prevented from firing the injector unless the tip of the injector is held against a surface.

DESCRIPTION OF THE PREFERRED EMBODIMENT

Figure 1:
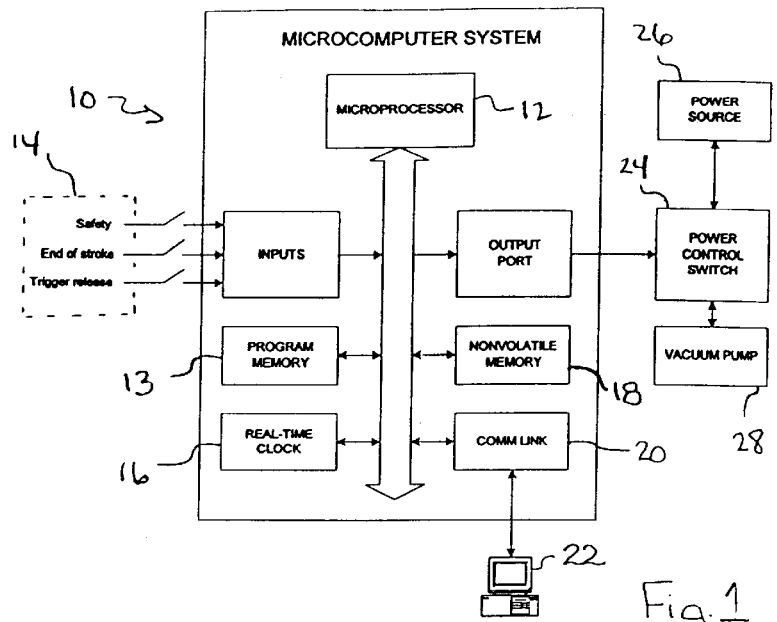
FIG. 1 is a schematic view of an integrated data logging and vacuum control system in accordance with the present invention.

Referring to FIG. 1, a system for injector data logging and injector vacuum control is shown schematically and generally designated 10. In overview, the system 10 includes a microcomputer having a microprocessor chip 12 and program memory 13 to process injection data. As further shown, one or more switches 14 which change state (e.g. from OFF to ON) during an injection procedure are input into the microcomputer system. These switches 14 can include a trigger release switch for indicating the start of an injection, an end-of-stroke switch for indicating the end of an injection and a safety switch. A real-time clock 16 is provided to establish the date and time in which the switches 14 change state.

Continuing with FIG. 1, the system 10 is shown to include a nonvolatile memory 18 (RAM) for storing the date and time corresponding to the change in state of switches 14. The date and time can be determined by a real time clock circuit or by software methods. The nonvolatile memory 18 can be either battery backed RAM or an EEPROM. After the data is stored in the nonvolatile memory 18, the stored data can be uploaded via a communications link 20 to a remote computer 22 for subsequent manipulation and analysis. In one implementation of the present invention, this analysis is conducted to determine a patient's compliance with a prescribed medicament dosing regimen. This analysis can include using the data to calculate the duration of an injection (the calculation can be performed by either the microprocessor 12 or the remote computer 22). This calculated injection duration can then be used to determine whether an injection event corresponds to a valid patient injection or an invalid firing (i.e. when the injector is fired into the air). The remote computer 22 can also be used to clear the nonvolatile memory 18 and set the initial date and time via the communications link 20.

In accordance with the present invention, the remote computer 22 is preferably a PC, such as an IBM compatible, and the communications link 20 can be implemented using conventional RS-232 serial, parallel, USB ports or by infrared or other wireless methods (e.g., bluetooth). Alternatively, an intermediary device (not shown) in the patient's home could be used to transmit injection data via modem to a remote computer 22 located at a Health Care Provider. It is to be further appreciated that the communications link 20 could be made using either a direct connection or via the Internet.

Referring still to FIG. 1, it can be seen that the system 10 includes a power control switch 24 to selectively deliver power from a power source 26 to an injector vacuum pump 28. In particular, the system 10 can be used to activate the vacuum pump 28 in response to a state change of a switch 14 (such as the closing of a safety switch prior to an injection). The system 10 can also be configured to deactivate the vacuum pump 28 in response to the change of state of a switch 14 (such as the end-of-stroke switch). Note: as described further below, the vacuum pump 28 can be used to provide suction at the injector tip to hold the injector against the patient's skin and create an advantageous subcutaneous pocket to receive the medicament.

The functional elements of the system 10, including the microprocessor 12, program memory 13, real-time clock 16, nonvolatile memory 18, the output port of the communications link 20, and the power control switch 24 may be integrated on one integrated circuit (IC) or on several IC's. Integrated circuits with a high degree of integration can allow an implementation requiring minimal space. One possible implementation is a single-chip microcontroller with either 4-bit or 8-bit word lengths. Low power versions are available with on-board program memory 13, real-time clock 16, input and output ports and communications ports for use in the communication link 20.

Figure 2:
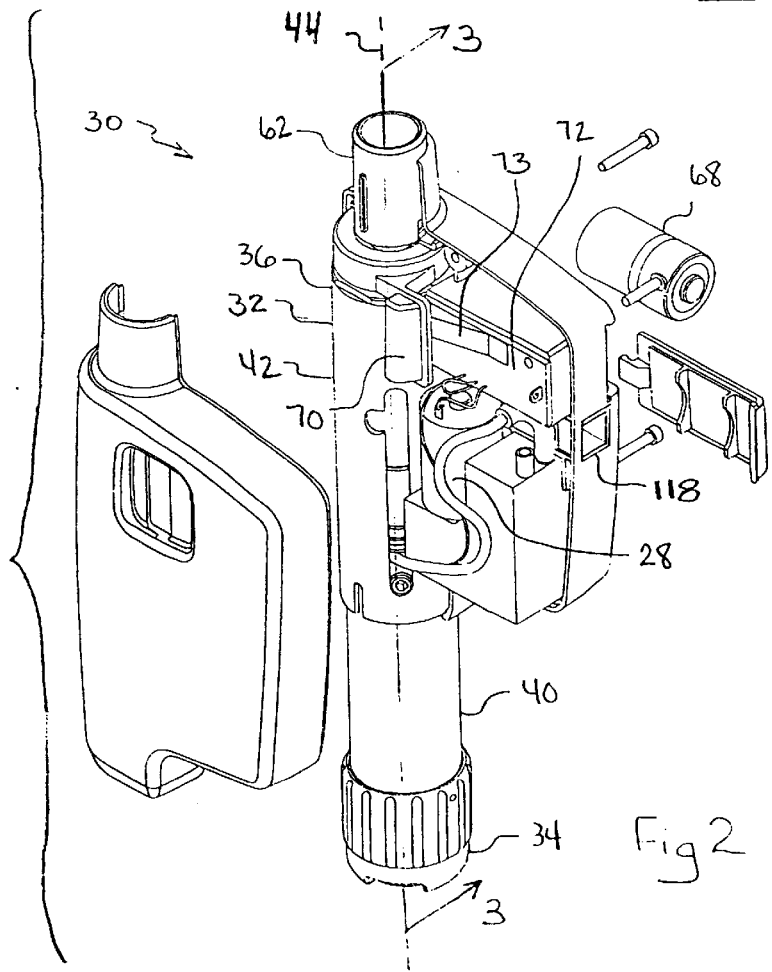
FIG. 2 is a perspective, partially exploded view of an injector having a data logging and vacuum control system in accordance with the present invention.

Referring now to FIG. 2, an injector 30 having data logging and vacuum control capability in accordance with the present invention is shown. As shown in FIG. 2, the injector 30 is formed with a tubular housing 32 having a distal end 34, and a proximal end 36. As further shown, the tubular housing 32 can include a hollow distal tube 40 and a hollow proximal tube 42, both centered on the axis 44, with the distal tube 40 being sized for insertion into the proximal tube 42.

Figure 3:
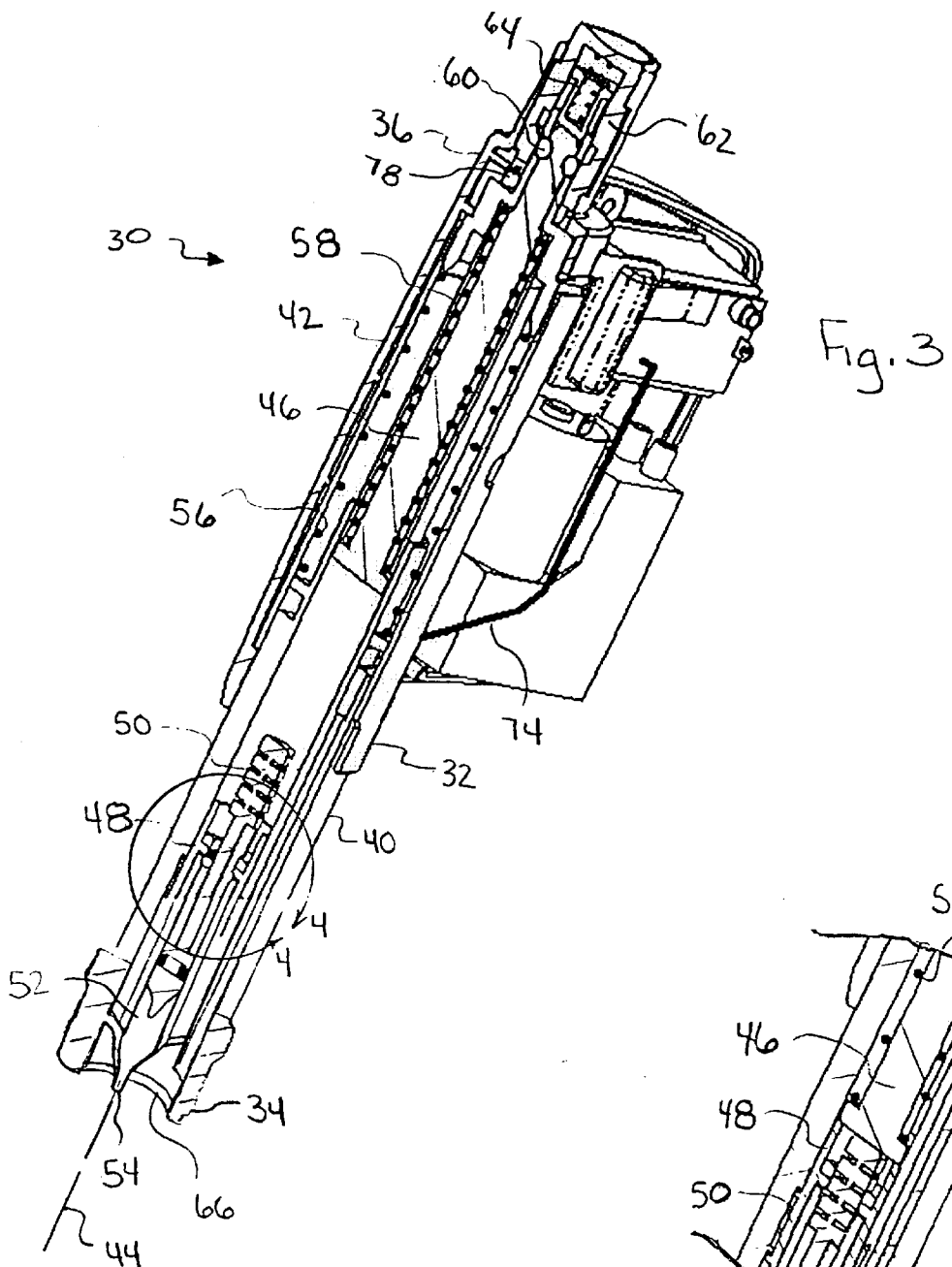
FIG. 3 is a perspective, cross-section view of the injector shown in FIG. 2 as seen along line 3—3 in FIG. 2, with the injector shown in the cocked configuration.

With cross reference now to FIGS. 2 and 3, it can be seen that a drive bar 46 is disposed within the housing 32 for movement along the longitudinal axis 44 during an injection. Further, as shown, an inner barrel 48 is positioned near the distal end 34 of the housing 32 to limit movement of the drive bar 46 in the distal direction at the completion of an injection. Also shown, a plunger 50 and a medicament chamber 52 are provided in the housing 32 at the proximal end 36. It is to be appreciated that the plunger 50 is insertable into the chamber 52 to expel fluid medicament from the chamber 52 and out through an injector tip 54.

Figure 4:
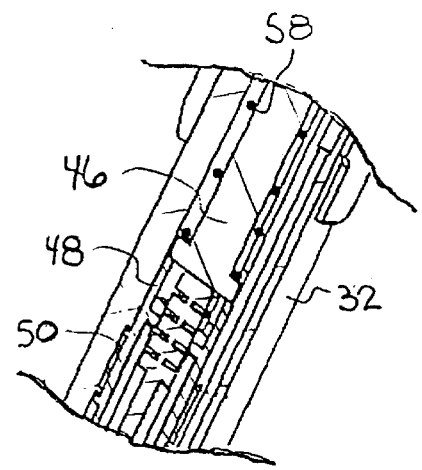
FIG. 4 is a perspective, cross-section view of a portion of the injector shown in FIG. 2 as seen along detail line 4—4 in FIG. 3, showing the drive bar in contact with the inner barrel after an injection.

With cross reference to FIGS. 3 and 4, it can be seen that the drive bar 46 translates within the housing 32 from a cocked position (shown in FIG. 3) to a post-injection position (shown in FIG. 4). For the present invention, the distal tube 40 is insertable into the proximal tube 42 to move the drive bar 46 into the cocked position (i.e. near the proximal end 36 of housing 32) immediately before an injection. A cocking return spring 56 is provided to reposition the distal tube 40 relative to the proximal tube 42 after cocking (i.e. to an uncollapsed position). Also shown, a mechanism such as a drive spring 58 is mounted inside the housing 32 for urging the drive bar 46 toward the distal end 34 of the housing 32.

With cross reference to FIGS. 2–4, it can be seen that the injector 30 includes a firing cap 62. As shown, the firing cap 62 is mounted on the housing 32 at the proximal end 36. Bearings 60, firing cap 62 and trigger spring 64 cooperate to engage the drive bar 46 during cocking and hold the drive bar 46 in the cocked position. It is to be appreciated that when the firing cap 62 is depressed by the user, the firing cap 62 disengages the bearings 60 and thereby releases the drive bar 46. Once the drive bar 46 is released, the force applied by the drive spring 58 is sufficient to translate the drive bar 46 along the longitudinal axis 44 of the housing 32 in the distal direction. By comparing FIGS. 3 and 4, it can be seen that the drive bar 46 is free to translate unhindered until the drive bar 46 impacts the plunger 50. The impact between the drive bar 46 and plunger 50 will force the plunger 50 into the medicament chamber 52, expelling medicament from the chamber 52 and through the injector tip 54. After impact, the drive bar 46 continues to translate in the distal direction, forcing the plunger 50 further into the chamber 52 to expel additional medicament, until the drive bar 46 finally contacts the inner barrel 48. Upon contact with the inner barrel 48, further travel of the drive bar 46 in the distal direction is prevented by the inner barrel 48. At this point, the drive spring 58 functions to hold the drive bar 46 against the inner barrel 48 until a subsequent injection is initiated by the user.

Referring now with cross reference to FIGS. 2 and 3, the injector 30 includes a vacuum system having a vacuum pump 28 for creating suction in a suction compartment 66 that surrounds the injector tip 54. As further shown, a battery 68 is provided to power the vacuum pump 28. Also shown, a vacuum ON/safety switch 70 that is user operable is included to control the vacuum pump 28. A printed circuit board 72 is provided containing a portion of an electrical circuit (shown in FIG. 5) that connects the battery 68 and vacuum pump 28 to the vacuum ON/safety switch 70. A return spring 73 is provided to bias the vacuum ON/safety switch 70 in the open (i.e. OFF) position.

For the present invention, the electrical circuit also includes an electrical connection to the drive bar 46 and an electrical connection to the inner barrel 48. Specifically, one lead from the electrical circuit is electrically connected to the proximal tube 42, which in turn, via drive spring 58, is in electrical contact with the drive bar 46. Further, as shown, wire 74 is provided to maintain an electrical connection between the inner barrel 48 and the electrical circuit on the printed circuit board 72. Importantly for the present invention, both the drive bar 46 and inner barrel 48 are constructed of electrically conductive materials. Preferably, the distal tube 40 is made of a nonconductive material such as plastic to insulate the inner barrel 48 from the proximal tube 42 when the drive bar 46 is not in contact with the inner barrel 48. With this cooperation of structure, contact between the drive bar 46 and inner barrel 48 acts as a switch (referred herein as the end-of-stroke switch 76) which closes at the end of an injection.

As best seen in FIG. 3, the electrical circuit also contains a connection to trigger release switch 78 which is positioned to close when the firing cap 62 is depressed. Thus, trigger release switch 78 closes at the start of an injection and opens after the injector 30 is cocked (i.e. when the firing cap 62 is replaced to its pre-firing, proximal position).

Figure 5:
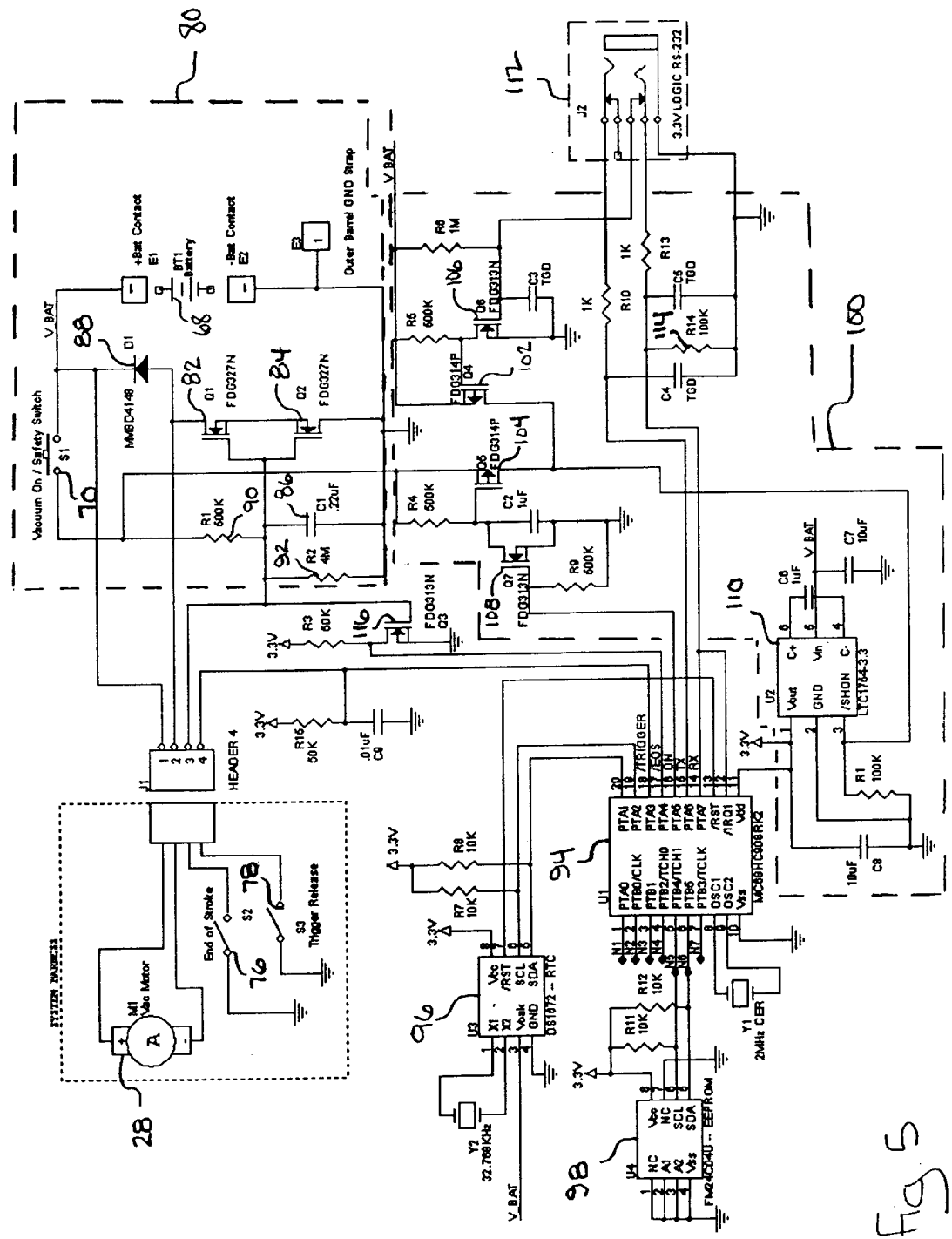
FIG. 5 is a schematic diagram of an electrical circuit for logging injector data and controlling an injector vacuum motor in accordance with the present invention.

A suitable electrical circuit for controlling the vacuum system and logging injection data in accordance with the present invention is shown schematically in FIG. 5. As shown, the circuit includes the vacuum ON/safety switch 70, the end-of-stroke switch 76, and the trigger release switch 78 described above.

Referring now to FIG. 5, it is to be appreciated that the electrical circuit includes a vacuum control circuit 80 that is configured to pass current from the battery 68 to the vacuum pump 28 when the vacuum ON/safety switch 70 is closed and the end-of-stroke switch 76 is open. Further, the vacuum control circuit 80 is configured to prevent current from passing through the vacuum pump 28 when the vacuum ON/safety switch 70 is open and the end-of-stroke switch 76 is closed. Additionally, the vacuum control circuit 80 is configured to prevent current from passing through the vacuum pump 28 whenever the vacuum ON/safety switch 70 is open.

To function in the manner described above, the vacuum control circuit 80 preferably includes a pair of MOSFET n type transistors 82, 84. Preferably, the transistors 82, 84 are both ultra low threshold (0.9 V) so that current can be passed to the vacuum pump 28 even when the battery 68 has emptied to below 2.0 V. Those skilled in the art will appreciate that only one MOSFET transistor 82, 84 is required to control the vacuum pump 28. The second MOSFET transistor 82, 84 is added to prevent damage to the first MOSFET transistor 82, 84 from excessive heat if the battery 68 is installed backwards.

A capacitor 86 is provided to hold the voltage at the gates of the transistors 82, 84 steady to ensure steady power to the vacuum pump 28. Diode 88 is provided to protect the transistors 82, 84 by shunting any negative kick generated by the effect of the inductance of the DC motor windings in the vacuum pump 28 in response to rapidly changing current. A large resistor 90 is provided to limit power loss when the vacuum ON/safety switch 70 and end-of-stroke switch 76 are both closed. Resistor 92 is provided in parallel to end-of-stroke switch 76 and capacitor 86. Resistor 92 biases the gate of the transistors 82, 84 such that they are non-conducting (vacuum pump 28 is off) when the vacuum ON/safety switch 70 is open. When the vacuum ON/safety switch 70 and end-of-stroke switch 76 are open, the gate is pulled low to ground through the resistor 92. The value of the resistor 92 is chosen such that with the selected value for resistor 90 and when the injector 30 is cocked and vacuum ON/safety switch 70 is closed and end-of-stroke switch 76 is open, the voltage at the gates of transistors 82, 84 is as close to the voltage of the battery 68 as possible.

In addition to the vacuum control circuit 80, the electrical circuit shown in FIG. 5 includes a microcontroller 94 having integrated program memory, RAM, input ports for sensing switch states, and output ports for transmitting and receiving data over a communication link. A real-time clock 96 provides date and time data when an injection is detected. This data is stored on a nonvolatile EEPROM memory 98. A power control system 100 consisting of transistors 102, 104, 106, 108 and charge pump IC 110 control the system power such that the microcontroller 94 is only turned on when needed and to minimize power usage during storage.

During storage (i.e. between injections), the electric circuit is configured to place the electrical circuit in a low-power sleep mode to conserve power. During the sleep state, only the real time clock 96, the vacuum ON/safety switch 70 and an activation circuit for the communications port 112 are energized. The quiescent power consumption of the activation circuit for the communications port 112 is approximately 3 uA (assuming a 3V battery) and the real time clock 96 consumes about 1 uA to keep time. Either one of two events could activate the microcontroller 94, namely, attaching a communications cable jack into the communications port 112 or closing the vacuum ON/safety switch 70. When the communications cable jack is inserted into the communications port 112, resistor 114 is removed from the gate of transistor 106 and it will turn on. Transistor 106 will then pull the gate of transistor 102 low, which applies V_BAT to enable the 3.3V charge pump 110. Charge pump 110 supplies the power to the microcontroller 94 and its peripherals. If the vacuum ON/safety switch 70 is closed, the charge pump 110 will be enabled as transistor 104 pulls the enable line to the battery voltage. The microcontroller 94 then has approximately 500 ms to complete its power up cycle and drive the ON signal high, which will turn on transistor 108 and hold the system power on. At the end of an injection the microcontroller 94 can turn itself off by pulling the ON line low.

During an injection, vacuum ON/safety switch 70 is pressed to start the vacuum pump 28 and power up the microcontroller 94. This pulls the gates of transistors 82 and 84 high, turning them on and starting the vacuum pump 28. Closing vacuum ON/safety switch 70 also turns on transistor 104, enabling power to the microcontroller 94. The user then depresses the firing cap 62 (shown in FIG. 2), which releases the drive bar 46 and closes the trigger release switch 78. At the end of the injection the drive bar 46 contacts the inner barrel 48 and thus closes the end of stroke switch 76. This pulls the charge off the gates of transistors 82, 84 and 116 to turn off the vacuum pump and turns off transistor 116, which indicates to the microcontroller 94 the end of the injection. The time between detecting the closure of the trigger release switch 78 to the closure of the end-of-stroke switch 76 can be calculated and indicates the duration of the injection. Once the microcontroller 94 records the data in the EEPROM memory 98, it turns itself off by pulling the ON line low. After an injection, the vacuum ON/safety switch 70, the end of stroke switch 76 and the trigger release switch 78 are all closed. This results in a quiescent drain of approximately 6 uA for end-of-stroke switch 76 closed, approximately 3 uA for the activation circuit for the communications port 112 and approximately. 1 uA for the real time clock 96 to keep time. A table of system status based on the state of the three switches can be seen in Table 1.

TABLE 1

| Switch 70 | Switch 76 | Switch 78 | System Status | Battery Current Drain |
| --- | --- | --- | --- | --- |
| closed | closed | closed | post injection sleep | 10 uA |
| closed | closed | open | cocking/transitioning | NA |
| closed | open | closed | injecting | <10 mA + motor current |
| closed | open | open | vacuum ON, ready to inject | <10 mA + motor current |
| open | closed | closed | invalid | NA |
| open | closed | open | cocking/transitioning | NA |
| open | open | closed | cocking/transitioning | NA |
| open | open | open | sleeping | 4 uA |

Preferably, the electrical circuit uses a microcontroller 94 that is a flash programmable, very low power device with on board flash ROM and static RAM. Furthermore, the microprocessor 94 preferably occupies a very small 20-pin USSOP package, to keep the PC board 72 (shown in FIG. 2) as small as possible. The microcontroller 94 shown in FIG. 5 operates using up to a 4 MHz clock and communicates with the EEPROM memory 98 and real time clock 96 using separate, standard 2-wire bus connections (standard IIC protocol). Pins 1–4 are attached to pads to allow for flash programming in circuit without overdriving any other component. The communications port 112 is preferably a RS-232 link, as shown in FIG. 5, and can be implemented on standard I/O lines and can achieve a maximum communications rate of 9600-baud using the 2 MHz crystal. As shown in FIG. 2, a communications receptacle 118 is provided on the injector 30 to accept an I/O line for electrical connection to the communications port 112.

Referring now to FIG. 6, it can be seen that user operable vacuum ON/safety switch 70 can also function as a safety release button for the firing cap 62. As shown, an interlock ring 120 can be mounted on the proximal end 36 of the housing 32 for rotation about the longitudinal axis 44 of the housing 32. As such, the interlock ring 120 is interposed between the proximal end 36 of the housing 32 and the firing cap 62. As further shown, the interlock ring 120 is attached to the vacuum ON/safety switch 70 for rotation about the longitudinal axis 44 of the housing 32 in response to movements of the vacuum ON/safety switch 70. A tab 122 projects proximally from the interlock ring 120 for interaction with a slot 124 formed in the firing cap 62. When the vacuum ON/safety switch 70 is depressed (i.e. closed), the interlock ring 120 is rotated to align the tab 122 of the interlock ring 120 with the slot 124 of the firing cap 62. With the tab 122 and slot 124 aligned, the firing cap 62 is armed (i.e. capable of being depressed to initiate an injection). The return spring 73, which biases the vacuum ON/safety switch 70 in the OFF position, also biases the interlock ring 120 into a position where the tab 122 and slot 124 are misaligned to thereby disarm and lock the firing cap 62 whenever the vacuum ON/safety switch 70 is not depressed.

Referring now to FIG. 7, an embodiment of an injector 126 in accordance with the present invention having a system for preventing invalid injections is shown. This system for preventing invalid injections is used in conjunction with the data logging and vacuum control system described above. Since invalid injections are prevented, invalid injections are not recorded by the data logging system, and thus, compliance with a prescribed dosage regimen can be accurately monitored. As shown in FIG. 7, the injector 126 includes a vacuum pump 128 to deliver a vacuum to a suction compartment 130. The suction compartment 130 is provided to hold the injector 126 against the surface 132 of the patient's skin during an injection and can be used to create a subcutaneous pocket to receive medicament from the injector 126.

In this embodiment, a vacuum sensor 134 monitors the vacuum downstream of the vacuum pump 128. It is to be appreciated that a significantly higher vacuum will be obtained downstream of the vacuum pump 128 and in the suction compartment 130 when the injector 126 is held against a surface 132 than when the injector 126 is not held against a surface 132 (i.e. when the injector 126 is oriented for firing into the air). Thus, the vacuum sensor 134 is configured to signal the actuator 136 when the vacuum level downstream of the vacuum pump 128 exceeds a pre-selected amount. Upon receipt of the signal from the vacuum sensor 134, the actuator 136 withdraws safety tab 138, arming firing cap 140.

Referring now to FIG. 8, another embodiment of an injector 142 in accordance with the present invention having a system for preventing invalid injections is shown. As shown in FIG. 8, the injector 142 includes a vacuum pump 144 to deliver a vacuum to a suction compartment 146. The suction compartment 146 is provided to hold the injector 142 against the surface 148 of the patient's skin during an injection and to create a subcutaneous pocket to receive medicament from the injector 142.

In the FIG. 8 embodiment, a current sensor 150 monitors the electrical current flowing through the motor of the vacuum pump 144. It is to be appreciated that motor current will increase due to a vacuum load on the vacuum pump 144. Thus, the current sensor 150 is configured to signal the actuator 152 when the pre-selected current flows through the motor of the vacuum pump (indicating that the injector 142 is being held against a surface 148). Upon receipt of the signal from the current sensor 150, the actuator 152 withdraws safety tab 154, arming firing cap 156. In an alternative embodiment of the present invention, the maximum current flowing through the vacuum pump 144 during an injection event is used to determine whether the injection event is a valid or invalid injection. In this alternative embodiment, invalid injections are not prevented, but rather are distinguished from valid injections by the compliance system.

Figure 9:
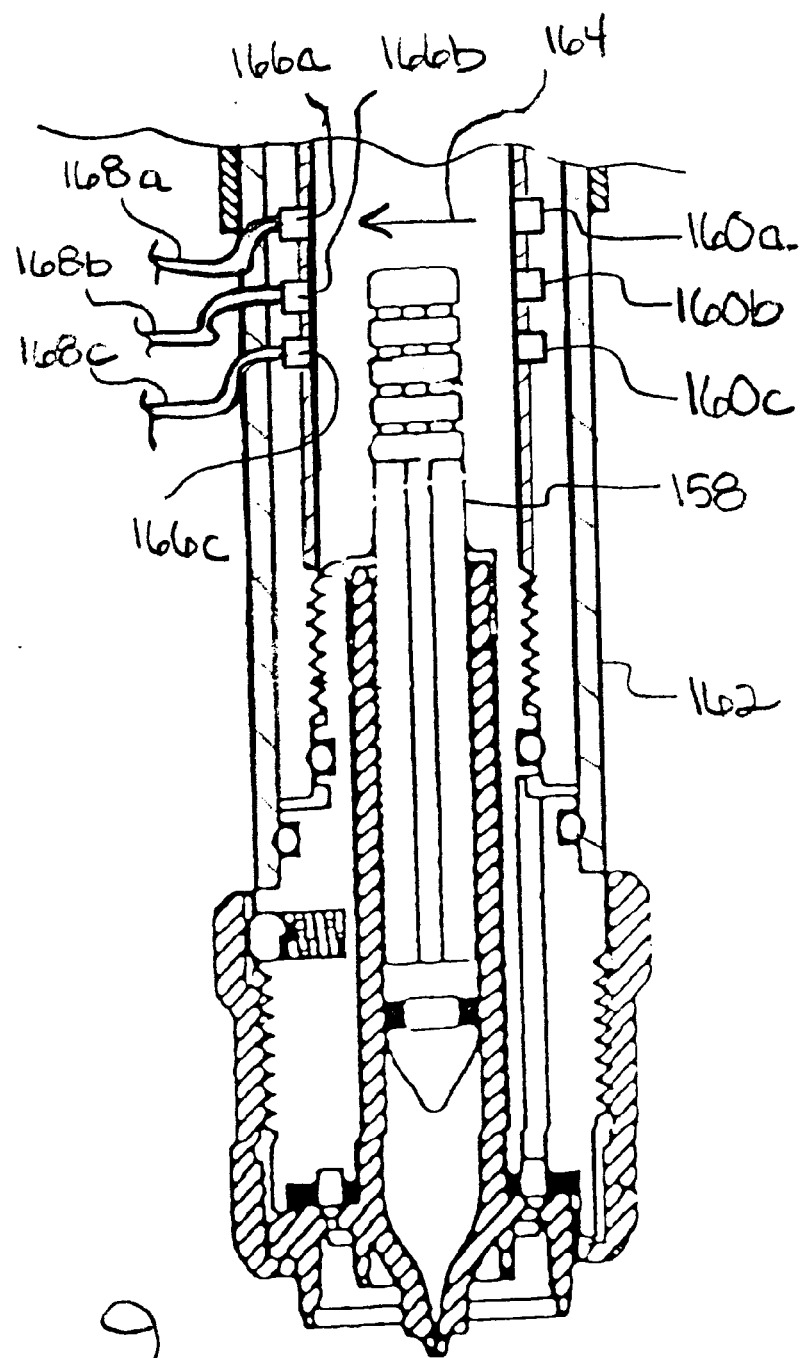
FIG. 9 is a sectional view as in FIG. 3 of another embodiment of the present invention in which light sensing switches are disposed inside the injector tube to determine the position of the syringe plunger immediately prior to an injection.

Referring now to FIG. 9, an embodiment of the present invention having a system for determining the position of the syringe plunger 158 immediately prior to an injection is shown. With the initial position of the syringe plunger 158, the dose amount for the respective injection can be calculated by the data logging system and used to determine compliance. As shown in FIG. 9, the system includes a plurality of light emitters 160, for which emitters 160a–c are exemplary, mounted in the distal tube 162 and positioned to emit light beams across the distal tube 162. Directional arrow 164 shows an exemplary path for a light beam emitted from emitter 160a. As further shown, the system includes a plurality of light sensing switches 166a–c that are disposed inside the distal tube 162 to receive a light beam from a respective emitter 160. It is to be appreciated that depending on the position of the syringe plunger 158, one or more of the light beams will be blocked and will not reach the corresponding light sensing switch 166. In this way, the position of the syringe plunger 158 can be determined. Sensor wires 168a–c transmit a signal from a respective light sensing switch 166 to the electrical circuit for processing by the data logging system to determine the dose amount for the injection.

While the particular device as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for determining the time duration ($\Delta t$) of an injection for use in a compliance monitoring program, said system comprising:

a fluid medicament injector having a first switch for changing states at the start of the injection and a second switch for changing states at the end of the injection; and an electronic clock connected to said first and second switches to establish an injection start time ($t_o$) in response to said first switch changing states and an injection end time ($t_e$) in response to said second switch changing states, said start time ($t_o$) and said end time ($t_e$) for calculating the time duration ($\Delta t$) where $\Delta t = t_e - t_o$; wherein said injector has a trigger to initiate the injection and said first switch is a trigger release.

2. A system as recited in claim 1 further comprising a microprocessor and electronic memory mounted on said injector to electronically store said injection start time ($t_o$) and said injection end time ($t_e$).

3. A system as recited in claim 2 wherein said microprocessor is configured to compare said time duration ($\Delta t$) to a predetermined time duration to determine whether the injection is valid.

4. A system as recited in claim 2 further comprising a communications link mounted on said injector to upload data stored in said electronic memory.

5. A system as recited in claim 1 wherein said injector comprises:
- a substantially hollow tube having a distal end and a proximal end;
- a conductive element positioned inside said tube near said distal end; and
- a conductive drive bar mounted inside said tube for distal movement during the injection from a first position near said proximal end to a second position in contact with said conductive element to close said second switch.

6. An integral vacuum control and data logging system for a fluid medicament injector having an injector tip, said system comprising:
- an electrical power source;
- a vacuum pump for producing a suction at the injector tip;
- at least one switch mounted on said injector for changing state during an injection procedure; and
- an electrical circuit for selectively passing a current from said power source to said vacuum pump and for establishing the time at which said switch changes states during the injection procedure, said time for use in a compliance monitoring program; wherein said at least one switch comprises a first switch for arming the injector, a second switch for changing state in response to the firing of the injector and a third switch for changing state upon the completion of an injection and wherein said electrical circuit is configured to pass current from said power source to said vacuum pump in response to a state change of said first switch and stop current flow to said vacuum in response to a state change of said third switch.

7. A system as recited in claim 6 wherein said time includes the date, hour and minute.

8. A system as recited in claim 7 wherein said injector is formed as a substantially hollow tube having a distal end and a proximal end, a conductive element is positioned inside said tube near said distal end, and a conductive drive bar is mounted inside said tube for distal movement during the injection from a first position near said proximal end to a second position in contact with said conductive element to close said third switch.

9. A system as recited in claim 6 wherein said electrical circuit comprises a microprocessor and electronic memory to electronically store said time.

10. A system as recited in claim 6 further comprising a communications link to upload data stored in said electronic memory.

11. A system for preventing injections from an injector having a tip when the injector tip is not in contact with a surface, said system for use in a compliance monitoring program, said system comprising:
- a safety mounted on said injector, said safety being reconfigurable between a first configuration wherein said injector is prevented from firing and a second configuration wherein said injector is armed;
- a vacuum pump for establishing a vacuum at the injector tip to hold the injector tip against the surface during an injection;
- a sensor for determining whether a predetermined vacuum level is present at the injector tip indicating that the injector tip is in contact with the surface; and
- a means responsive to said sensor for reconfiguring said safety to arm said injector when said predetermined vacuum level is present at the injector tip; wherein said sensor measures a vacuum level to determine whether said predetermined vacuum level is present at the injector tip.

12. A system as recited in claim 11 wherein said reconfiguring means comprises a pneumatic actuator.

13. A system as recited in claim 11 wherein said injector includes a firing cap to initiate an injection and said safety prevents movement of the firing cap when said safety is in said first configuration.

14. A system for preventing injections from an injector having a tip when the injector tip is not in contact with a surface, said system for use in a compliance monitoring program, said system comprising:
- a safety mounted on said injector, said safety being reconfigurable between a first configuration wherein said injector is prevented from firing and a second configuration wherein said injector is armed;
- a vacuum pump for establishing a vacuum at the injector tip to hold the injector tip against the surface during an injection;
- a sensor for determining whether a predetermined vacuum level is present at the injector tip indicating that the injector tip is in contact with the surface; and
- a means responsive to said sensor for reconfiguring said safety to arm said injector when said predetermined vacuum level is present at the injector tip;
- wherein said sensor measures a motor current of said vacuum pump to determine whether said predetermined vacuum level is present at the injector tip.

* * * * *

UNITED STATES PATENT AND TRADEMARK OFFICE
CERTIFICATE OF CORRECTION

PATENT NO.   : 6,817,986 B2
DATED        : November 16, 2004
INVENTOR(S)  : John B. Slate, Michael W. Burk and Lanny A. Gorton It is certified that error appears in the above-identified patent and that said Letters Patent is hereby corrected as shown below:

Column 10,
Line 67, insert -- switch. -- to be inserted after the word "release" but before the "."

Signed and Sealed this

Twenty-second Day of March, 2005

JON W. DUDAS
*Director of the United States Patent and Trademark Office*